United States Patent
Olds et al.

(10) Patent No.: US 10,646,990 B2
(45) Date of Patent: May 12, 2020

(54) DELTA MECHANISM WITH ENHANCED TORSIONAL STIFFNESS

(71) Applicant: The Johns Hopkins University, Baltimore, MD (US)

(72) Inventors: Kevin C. Olds, Baltimore, MD (US); Russell H. Taylor, Severna Park, MD (US)

(73) Assignee: The Johns Hopkins University, Baltimore, MD (US)

(*) Notice: Subject to any disclaimer, the term of this patent is extended or adjusted under 35 U.S.C. 154(b) by 172 days.

(21) Appl. No.: 15/213,189

(22) Filed: Jul. 18, 2016

(65) Prior Publication Data

US 2018/0000548 A1    Jan. 4, 2018

Related U.S. Application Data

(60) Provisional application No. 62/194,013, filed on Jul. 17, 2015.

(51) Int. Cl.
*B25J 9/00* (2006.01)
*A61B 34/30* (2016.01)
(Continued)

(52) U.S. Cl.
CPC ....... *B25J 9/0051* (2013.01); *A61B 2034/304* (2016.02); *B25J 9/1689* (2013.01); *B25J 13/085* (2013.01)

(58) Field of Classification Search
CPC ........ B25J 9/0051; B25J 9/1689; B25J 9/003; B25J 9/106; B25J 9/1623; B25J 17/0241;
(Continued)

(56) References Cited

U.S. PATENT DOCUMENTS

| 4,976,582 | A | 12/1990 | Clavel |
| 5,397,323 | A | 3/1995 | Taylor et al. |
| 5,887,121 | A | 3/1999 | Funda et al. |
| 6,575,676 | B2 * | 6/2003 | Wang ............ B23Q 1/5462 |
| | | | 409/201 |

(Continued)

FOREIGN PATENT DOCUMENTS

| DE | 102004058450 A1 * | 6/2006 | ........... B08B 9/045 |
| FR | 2896847 A1 * | 8/2007 | ............ B25J 9/06 |
| WO | WO-2015115887 A1 * | 8/2015 | .......... B25J 9/0075 |

OTHER PUBLICATIONS

Bonev, "Delta Parallel Robot—the Story of Success." http://www.parallemic.org/Reviews/Review002.html. (May 2001).
(Continued)

*Primary Examiner* — Bobby Rushing, Jr.
(74) *Attorney, Agent, or Firm* — Venable LLP; Henry J. Daley

(57) ABSTRACT

A mechanical translation apparatus includes a translation stage and a translation assembly operatively connected to the translation stage so as to impart linear motions to the translation stage substantially free of rotational motions. The translation assembly includes a plurality of at least three arms pivotably connected to the translation stage at a first end of each arm of the plurality of at least three arms. The mechanical translation apparatus also includes a base assembly in which each arm of the plurality of at least three arms is also rotationally connected to the base assembly at a second end of each arm. Each arm of the plurality of at least three arms includes three rigid elongate structures arranged substantially parallel and non-coplanar with respect to each other so as to act in cooperation to cancel torques so that substantially purely linear motion is imparted to the translation stage by the plurality of at least three arms, and the translation assembly constrains motion of the translation stage to be substantially purely translational motion free of
(Continued)

rotational motion. A robot includes the mechanical translation apparatus.

12 Claims, 16 Drawing Sheets

(51) Int. Cl.
  *B25J 13/08* (2006.01)
  *B25J 9/16* (2006.01)
(58) Field of Classification Search
  CPC .. B25J 17/025; B25J 17/0258; B25J 17/0266;
              B25J 17/0275; B25J 17/0283; A61B
              2034/304; A61B 34/35
  USPC .......................................................... 403/54
  See application file for complete search history.

(56) References Cited

U.S. PATENT DOCUMENTS

| | | | | |
|---|---|---|---|---|
| 6,766,711 | B2* | 7/2004 | Hvittfeldt | B25J 17/0266 74/490.03 |
| 6,976,821 | B2* | 12/2005 | Zarske | B25J 9/0051 340/12.22 |
| 7,594,912 | B2 | 9/2009 | Cooper et al. | |
| 7,938,602 | B2* | 5/2011 | Ota | B23Q 1/4857 409/201 |
| 8,272,290 | B2* | 9/2012 | Zhang | B25J 9/107 74/490.01 |
| 8,318,094 | B1* | 11/2012 | Bayandorian | G01N 21/645 422/400 |
| 8,911,429 | B2 | 12/2014 | Olds et al. | |
| 9,566,708 | B2* | 2/2017 | Kurnianto | B25J 9/02 |
| 2004/0086351 | A1* | 5/2004 | Kim | B23Q 1/34 409/235 |
| 2011/0097184 | A1* | 4/2011 | Kinoshita | B25J 17/0266 414/589 |
| 2015/0343631 | A1* | 12/2015 | Martinez-Esponda | B25J 9/0051 74/490.03 |
| 2016/0214303 | A1* | 7/2016 | Gerstenhaber | D01D 5/0061 |
| 2017/0210067 | A1* | 7/2017 | Gajkowski | B29C 67/005 |

OTHER PUBLICATIONS

Funda et al., "Constrained Cartesian motion control for teleoperated surgical robots", IEEE Transactions on Robotics and Automation, vol. 12-3, pp. 453-466 (1996).

Iordachita et al., "Steady-Hand Manipulator for Retinal Surgery", in MICCAI Workshop on Medical Robotics, Copenhagen, Oct. 5, 2006, pp. 66-73.

Kapoor et al., "A Constrained Optimization Approach to Virtual Fixtures for Multi-Handed Tasks," in IEEE International Conference on Robotics and Automation (ICRA), Pasadena, May 19-23, 2008, pp. 3401-3406.

Kapoor et al., "Simple Biomanipulation Tasks with a "Steady Hand" Cooperative Manipulator," in Proceedings of the Sixth International Conference on Medical Image Computing and Computer Assisted Intervention—MICCAI 2003, Montreal, Nov. 15-18, 2003, pp. 141-148.

Kapoor et al., "Telemanipulation of Snake-Like Robots for Minimally Invasive Surgery of the Upper Airway," in MICCAI Medical Robotics Workshop, Copenhagen, Oct. 2006, 9 pages.

Kumar et al., "Performance of Robotic Augmentation in Microsurgery-Scale Motions", in 2nd Int. Symposium on Medical Image Computing and Computer-Assisted Surgery, Cambridge, England, 1998, pp. 1108-1115.

Leuth et al., "A Surgical Robot for Maxillofacial Surgery," IEEE Industrial Electronics Conference, 1998, pp. 2470-2475.

Li et al., "Performance of Teleoperated and cooperatively controlled surgical robots with automatically generated spatial virtual fixtures.", in IEEE International Conference on Robotics and Automation, Barcelona, Spain, 2005, pp. 217-222.

Li et al., "A Constrained Optimization Approach to Virtual Fixtures," in IEEE/RSJ Int Conf on Intelligent Robots and Systems (IROS), Edmonton, Alberta, Canada, 2005, 6 pages.

Li et al., "Spatial Motion Constraints in medical Robot Using Virtual Fixtures Generated by Anatomy," IEEE Conference on Robotics and Automation, 2004, pp. 1270-1275.

Li et al., "Spatial Motion Constraints Using Virtual Fixtures Generated by Anatomy," IEEE Transactions on Robotics, vol. 31, No. 1, pp. 4-19 (2007).

Li et al., "Telerobotic Control by Virtual Fixtures for Surgical Applications," Advances in Telerobotics Human Interfaces, Bilateral Control and Applications, M. Ferre, M. Buss, R. Aracil, C. Melchiorri, and C. Balaguer, Eds., pp. 381-401 (2007).

Simaan et al., "Design and Integration of a Telerobotic System for Minimally Invasive Surgery of the Throat," Int. J. Robotics Research, pp. 1-20 (2009).

Taylor et al., "A Steady-Hand Robotic System for Microsurgical Augmentation", International Journal of Robotics Research, vol. 18, No. 12, pp. 1201-1210 (1999).

Tsumaki et al., "Design of a Compact 6-DQF Haptic Interface," Proceedings of the 1998 IEEE International Conference on Robotics & Automation Leuven, Belgium, pp. 2580-2585 (1998).

* cited by examiner

DELTA MECHANISM WITH ENHANCED TORSIONAL STIFFNESS

This application claims priority to Provisional Application No. 62/194,013, filed Jul. 17, 2015.

BACKGROUND

1. Technical Field

The field of the currently claimed embodiments of this invention relates to delta mechanisms, robotic systems that include delta mechanisms, and to cooperative-control robots and systems that include delta mechanisms.

2. Discussion of Related Art

Many surgical disciplines such as ophthalmology, otology, laryngology, neurosurgery, and cosmetic and reconstructive surgery, as well as non-surgical fields such as bio-medical research and micro assembly, have a micro manipulation component that pushes human sensory-motor limits. Several robotic solutions have been proposed to solve similar problems in surgery, most prominently the daVinci surgical robot from Intuitive surgical (FIG. 1). The daVinci robot was primarily designed for minimally invasive surgery, and uses a teleoperation control paradigm. This means that the control console and the robot itself are separate pieces of equipment, and the surgeon sits away from the patient.

Though the teleoperation paradigm presents many advantages in minimally invasive surgery, it presents little benefit in many microsurgical tasks. Separating the robot and console causes the whole system to have a much larger operating room (OR) footprint, and unnaturally removes the surgeon from the operation area. The overall bulk of the system makes it time consuming to set up and disengage, so it is difficult to bring it in and out of the OR as needed. Also, since the daVinci robot is designed to mimic the natural hand position of surgeons performing minimally invasive surgery, it has difficulty operating with instrument shafts parallel to each other, as in laryngeal surgery. These limitations can also result in the need to completely change surgical practices in order to accommodate the robot. Another major drawback of this system is its cost. The daVinci robot has both high fixed costs (initial robot cost ~$2 million) and high variable costs (custom disposable surgical instruments, surgical training for daVinci operations).

Since the daVinci robot is mostly used in minimally invasive surgery, it is designed to operate through small incisions. This requires its instruments to pivot about the point where they enter the patient, so as not to put forces on the incision. This is called a remote center of motion (RCM), since the tool is rotating about a point that is outside of the robot. The daVinci robot achieves two rotational degrees of freedom (tilt and roll) about a remote center of motion using a rotation stage and a cable mechanism (FIG. 2). It also has a translational degree of freedom to insert and withdraw tools along the tool axis. This translation mechanism is at the end of the arm, which adds significant bulk and prevents the robot from operating with two instruments parallel to each other and in close proximity (FIG. 3).

Another approach to overcoming human sensorimotor limitations in surgery has been taken by the JHU Eye Robot 2 (FIG. 4). This system uses a cooperative control paradigm where the surgeon sits with the patient and holds the surgical tool along with the robot. The robot senses the surgeon's pressure on the tool through a force sensor and moves accordingly. This system is much smaller and requires less modification to surgical procedures than the daVinci robot.

The JHU Eye Robot 2 uses three translation stages to give x, y, and z translational degrees of freedom, as well as a rotation stage and a remote center of motion linkage[2] to provide the necessary rotational degrees of freedom. If the tool needs to rotate about a point that is different from the rotation center of the mechanisms, then the translation stages can compensate and allow the tool's shaft to rotate about another point. The main limitation of this design is that it relies on a fundamentally serial mechanism, which requires each actuator to carry all subsequent actuators. This makes the overall system larger and heavier than it would otherwise need to be. The weight of the robot imposes speed limits on the translation stages, which in turn prevents them from tracking fast surgical motions, or compensating for centers of motion that are far from that of the mechanism.

An earlier version of the JHU Eye Robot 2, the JHU Eye Robot 1, used a standard 4-bar linkage rather than the remote center of motion linkage, a rotation stage, and a similar 3 degree of freedom (dof) set of translation stages (FIG. 5). The mechanism has no natural RCM point, and uses the translation stages to augment the rotation joints and provide RCM functionality. The RCM linkage was added in the JHU Eye Robot 2 because the translation stages in the serial design were too slow to compensate for the RCM point needed in eye surgery.

Alternative mechanisms for providing three degree of freedom translational motion exist, most notably the delta mechanism (FIG. 6). This mechanism uses three parallelogram linkages in parallel to provide x, y, and z translational degrees of freedom, as well as an extending shaft with two universal joints to provide an additional rotational degree of freedom, for a total of four degrees of freedom. An advantage of this mechanism is that the actuators act in parallel, meaning that they do not need to carry each other's mass. Because of this, the delta mechanism has been used extensively in industrial robotics for high-speed pick and place applications, as well as for surgical applications, and haptic master control (FIG. 7).

The delta mechanism has been used in surgical applications, most notably in maxillofacial surgery (FIG. 8).[6] This system, the ISIS Surgiscope, is a large overhead delta robot designed to manipulate a surgical microscope, which was modified to manipulate surgical tools such as bone drills. It uses a force sensor to detect interaction forces between tools and tissue. Rather than a cooperative control paradigm, this system uses an "interactive planning, programming and teaching" scheme where the robot's freedom is restricted using limits on position, orientation, force, and torque. This system uses motors mounted on the delta robot's mobile platform ((8) in FIG. 6) to control the surgical tools.

This system is not well suited to microsurgery, due to its large size and mass. Also, since it is so large and ceiling mounted, it would not be feasible for two such systems to work together in a bimanual operation. The largely planned and pre-determined operating method this system uses would not be useful in surgeries without extensive preoperative imaging, registration, and rigid anatomy.

The delta mechanism has also been modified to integrate additional actuators into the arms of the system for the purpose of powering additional degrees of freedom at the tip (FIG. 9).[7] A variant of the delta robot which uses linear actuators was also proposed in the original delta robot (FIG. 10).

However, the conventional delta mechanisms have low stiffness against applied torques. There thus remains the need for improved delta mechanisms and robotic systems that incorporate such improved delta mechanisms.

SUMMARY

A mechanical translation apparatus according to an embodiment of the current invention includes a translation stage and a translation assembly operatively connected to the translation stage so as to impart linear motions to the translation stage substantially free of rotational motions. The translation assembly includes a plurality of at least three arms pivotably connected to the translation stage at a first end of each arm of the plurality of at least three arms. The mechanical translation apparatus also includes a base assembly in which each arm of the plurality of at least three arms is also rotationally connected to the base assembly at a second end of each arm. Each arm of the plurality of at least three arms includes three rigid elongate structures arranged substantially parallel and non-coplanar with respect to each other so as to act in cooperation to cancel torques so that substantially purely linear motion is imparted to the translation stage by the plurality of at least three arms, and the translation assembly constrains motion of the translation stage to be substantially purely translational motion free of rotational motion.

A robot according to an embodiment of the current invention includes a translation stage, a translation assembly operatively connected to the translation stage so as to impart linear motions to the translation stage substantially free of rotational motions, wherein said translation assembly comprises a plurality of at least three arms pivotably connected to the translation stage at a first end of each arm of the plurality of at least three arms. The robot also includes a base assembly wherein each arm is rotationally connected thereto at a second end of each arm, and a control system configured to communicate with the translation assembly to control motion of the translation stage in response commands by a user. Each arm of the plurality of at least three arms includes three rigid elongate structures arranged substantially parallel and non-coplanar with respect to each other so as to act in cooperation to cancel torques so that substantially purely linear motion is imparted to the translation stage by the plurality of at least three arms. The translation assembly constrains motion of the translation stage to be substantially purely translational motion free of rotational motion.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

The current inventors had previously developed cooperative control robots that include delta mechanisms. See U.S. application Ser. No. 13/669,176, now U.S. Pat. No. 8,911,429, which issued on Dec. 16, 2014, and is assigned to the same assignee as the current application, the entire contents of which are incorporated herein by reference. Some embodiments of the current invention include improved robotic systems that include the new delta mechanism described herein. However, the general concepts of the current invention are not limited to only those embodiments.

Figure 11:
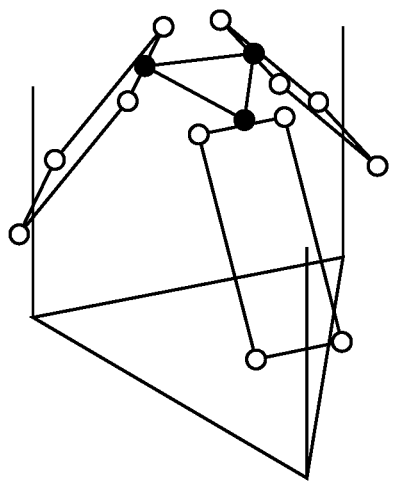
FIG. 11 is a schematic illustration of a conventional linear delta mechanism.

Some embodiments of the current invention are directed to preventing unwanted rotation of the mobile platform of a delta mechanism. FIG. 11 shows a schematic illustration of a linear version of a conventional delta mechanism. In the following figures, black circles represent rigid connections, white circles are ball joints, and white cylinders are rotary joints. The mobile platform is represented by the small triangular structure at the top of the device.

Figure 12:
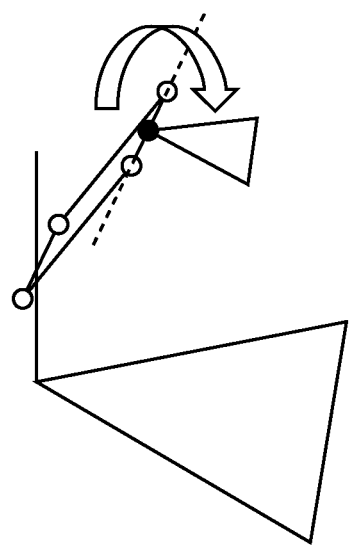
FIG. 12 is a schematic illustration to help explain that one leg of a conventional delta mechanism cannot resist torsional load.

Problems arise when a torsional load is applied to the mobile platform. In the conventional design, each one of the three legs alone is not able to resist rotation of the mobile platform. FIG. 12 shows this case for one leg. Only when the constraints of all three legs are combined together can the mechanism resist torsional load on the mobile platform. This compromises the torsional stiffness of the mechanism as a whole.

Figure 13:
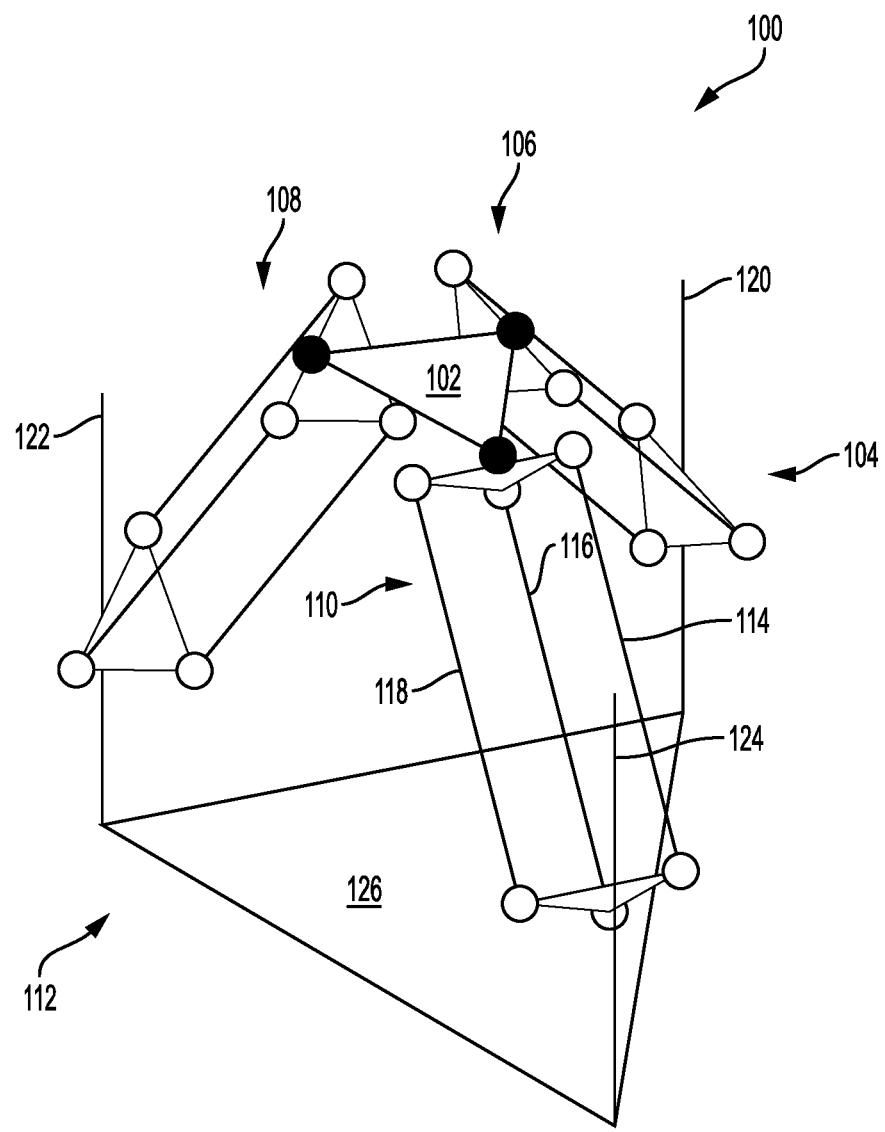
FIG. 13 is a schematic illustration of a delta mechanism according to an embodiment of the current invention in which each leg alone can resist torsional load (also see FIG. 14).
Figure 14:
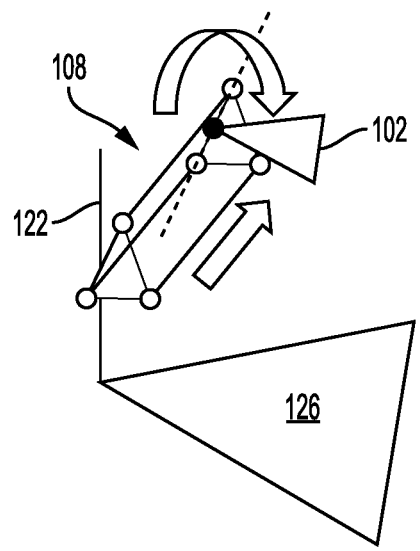
FIG. 14 is a schematic illustration of a portion of the embodiment of FIG. 13 to help explain some concepts of the current invention. The torsional load (circular arrow) is offset by the force in the third beam (straight arrow).

An embodiment of the current invention adds a third beam to the parallelogram of each leg in order to alleviate this problem as is illustrated schematically in FIG. 13. Using this new design, each leg alone can resist torsional load as is illustrated schematically in FIG. 14.

Figure 15:
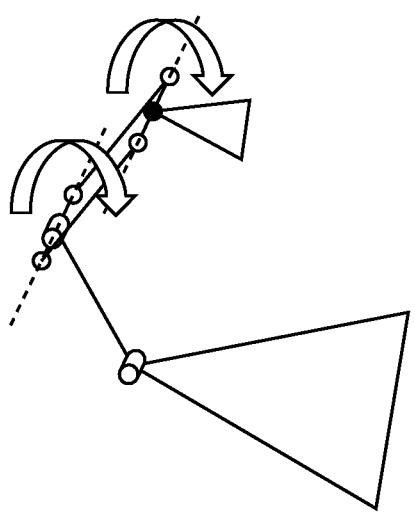
FIG. 15 is a schematic illustration of one leg of a conventional rotary delta mechanism to help explain how it fails to resist a torsional load.
Figure 16:
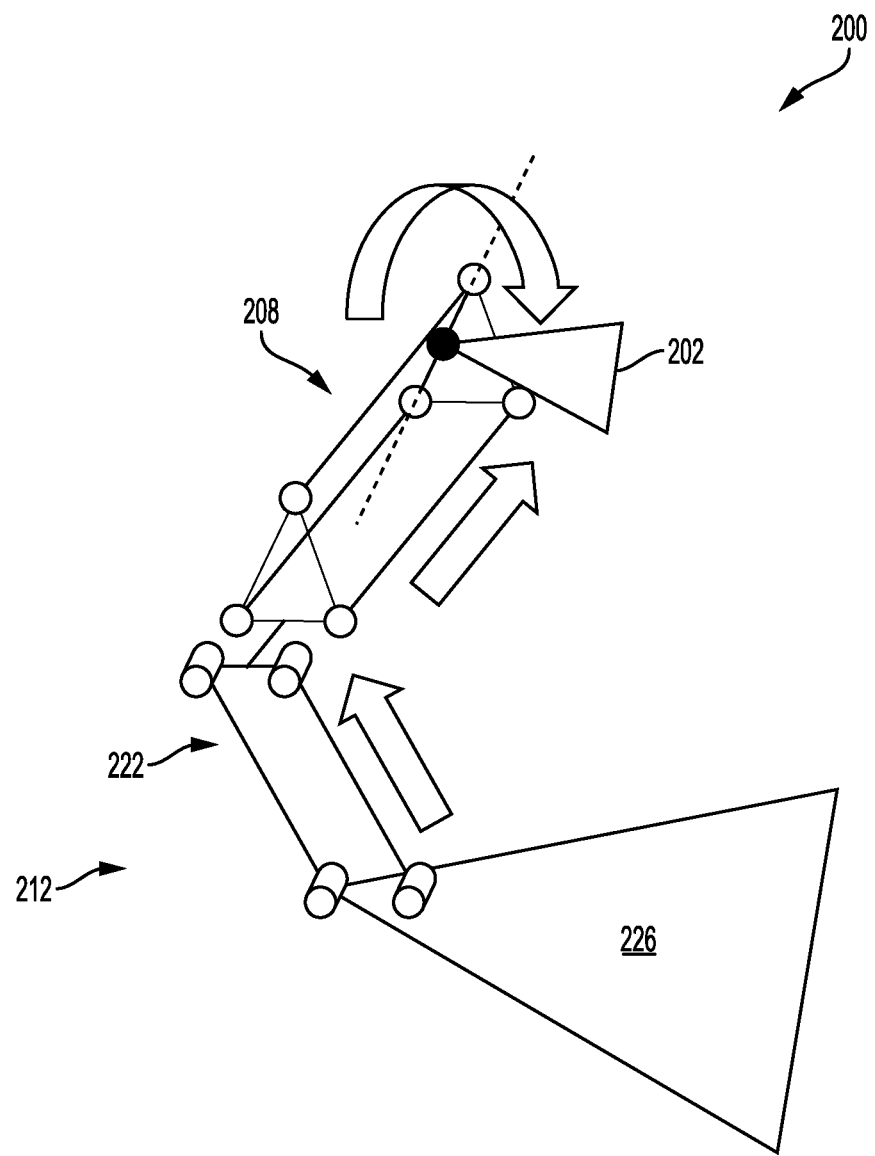
FIG. 16 is a schematic illustration of one leg of a rotary delta mechanism according to an embodiment of the current invention explaining that it can resist torsional loads.

Other embodiments can be provide a rotary variant of the delta mechanism. One leg of the conventional rotary variant also cannot resist torsional load as is illustrated schematically in FIG. 15. By adding a third parallelogram beam according to this embodiment of the current invention, similar to the above-described embodiment, as well as a second primary beam, each leg of the rotary delta mechanism can also independently resist torsional loads (FIG. 16).

Accordingly, FIG. 13 provides a schematic illustration of a mechanical translation apparatus 100 according to an embodiment of the current invention. The mechanical translation apparatus 100 includes a translation stage 102 and a translation assembly 104 operatively connected to the translation stage 102 so as to impart linear motions to the translation stage 102 substantially free of rotational motions. The translation assembly 104 includes a plurality of at least three arms (106, 108, 110) pivotably connected to the translation stage at a first end of each arm of the plurality of at least three arms (106, 108, 110). The mechanical translation apparatus 100 also includes a base assembly 112 in which each arm (106, 108, 110) is rotationally connected thereto at a second end of each arm (106, 108, 110). Each arm, for example arm 110, of the plurality of at least three arms (106, 108, 110) includes three rigid elongate structures (114, 116, 118) arranged substantially parallel and non-coplanar with respect to each other so as to act in cooperation to cancel torques so that substantially purely linear motion is imparted to the translation stage 102 by the plurality of at least three arms (106, 108, 110). The translation assembly 104 constrains motion of the translation stage 102 to be substantially purely translational motion free of rotational motion.

In some embodiments, the base assembly 112 includes three substantially parallel, non-coplanar track assemblies (120, 122, 124) extending from a base structure 126. Each of the three track assemblies (120, 122, 124) is configured to receive a corresponding one of the arms of the plurality of at least three arms (106, 108, 110) such that each arm is slidable along a respective track of the track assemblies (120, 122, 124) as well as being rotatable about an axis substantially orthogonal to a direction of the track extending from the base structure 126.

In some embodiments, each track assembly includes an actuator to drive motion of a corresponding one of the at least three arms (106, 108, 110) along the direction of the corresponding track.

In some embodiments, as is illustrated schematically in FIG. 16, the base assembly 212 includes a plurality of secondary arms, such as secondary arm 222 instead of the track assemblies 120, 122, 124. Each secondary arm of the base assembly 212 is rotationally connected at one end to a corresponding arm, which can be the same or similar to arms 106, 108, 110, and also rotationally connected at a second end to base structure 226 of the base assembly 212. FIG. 16 is a schematic illustration of a portion of such an embodiment. Each secondary arm can include a pair of substantially parallel elongate structures, as is shown for secondary arm 222. Arm 208 can be the same as or similar to arm 108 in some embodiments.

Figure 17:
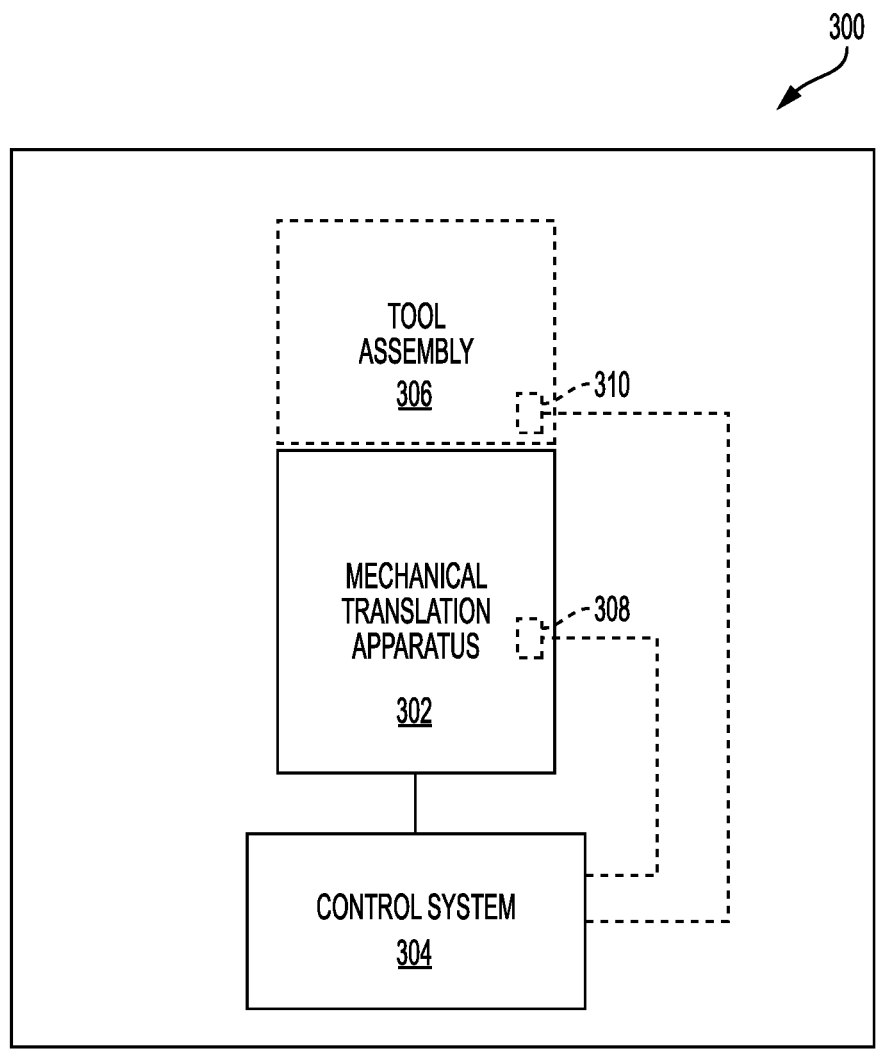
FIG. 17 is a schematic illustration of a cooperative control robot according to an embodiment of the current invention.

Some embodiments of the current invention are directed to cooperative control robots. Surgical robots will be referred to with respect to some embodiments. However, the general concepts of the current invention are not limited to only surgical robots. Other embodiments can be other types of robots applied to industrial processes, manufacturing, micro-assembly, etc. FIG. 17 is a schematic illustration of a cooperative control robot 300 according to an embodiment of the current invention. The cooperative control robot 300 has a mechanical translation apparatus 302 according to an embodiment of the current invention, such as, but not limited to mechanical translation apparatus 100 or 200. The cooperative control robot 300 also has a control system 304 configured to communicate with the mechanical translation apparatus 302 so as to provide it with controls signals. In some embodiments, the cooperative control robot 300 can also have a tool assembly 306 attached to the translation stage of the translation apparatus (such as, but not limited to, 102 and/or 202) to be carried along with the translation stage. The tool assembly 306 and/or the mechanical translation assembly 302 can have one or more force sensors (308, 310) configured to detect forces applied by a user and to communicate those detected forces to the control system 304. The tool assembly 306 can also include a tool holder in some embodiments. The control system 304 is configured to communicate with the translation assembly to control motion of the translation stage 102 or 202 in response to forces by a user applied to at least a portion of the cooperative-control robot. The control system can be integrated into the base assembly and/or a separate component, for example.

Some embodiments of robotic systems according to the current invention can further include a user input device adapted to communicate with the control system to at least one of interrupt or supplement cooperative control. The user input device can be, but is not limited to, a foot peddle, for example.

Some embodiments of the current invention can include two or more cooperative-control robots. The cooperative-control robots can be positioned so that a surgeon can operate with each hand, thus providing bimanual surgical capability. In some embodiments, the system could include a hands-on cooperative control paradigm, similar to the JHU "steady hand" robots. In this case, a force sensor attached to the tool holder, or to a control handle attached to the tool holder or to the surgical tool itself, would sense forces exerted by the surgeon on the tool, and the robot controller would cause the robot to move to comply with these forces. In this case, the surgeon can have the impression that he or she is manipulating the tool in much the same way as in normal surgery. But since the robot is doing the actual moving of the tool, there will be no, or at least substantially reduced, hand tremor. Also, if the surgeon releases the tool, the tool can simply stop moving, rather than fall as it would in normal surgery.

The robotic systems according to some embodiments may also be teleoperated from master control arms such as those used to control the DaVinci surgical robot or from simpler master control arms such as the Sensable Technology Omni arms, or from multiple joysticks, or from other master control arms. In this case, forces exerted on the tools sensed in the force sensors can be "fed back" to the master control arms to provide haptic feedback or to otherwise modify the motion of the robot. Also, the control modes may be mixed or switched between teleoperation control and hands-on cooperative control.

Figure 18:
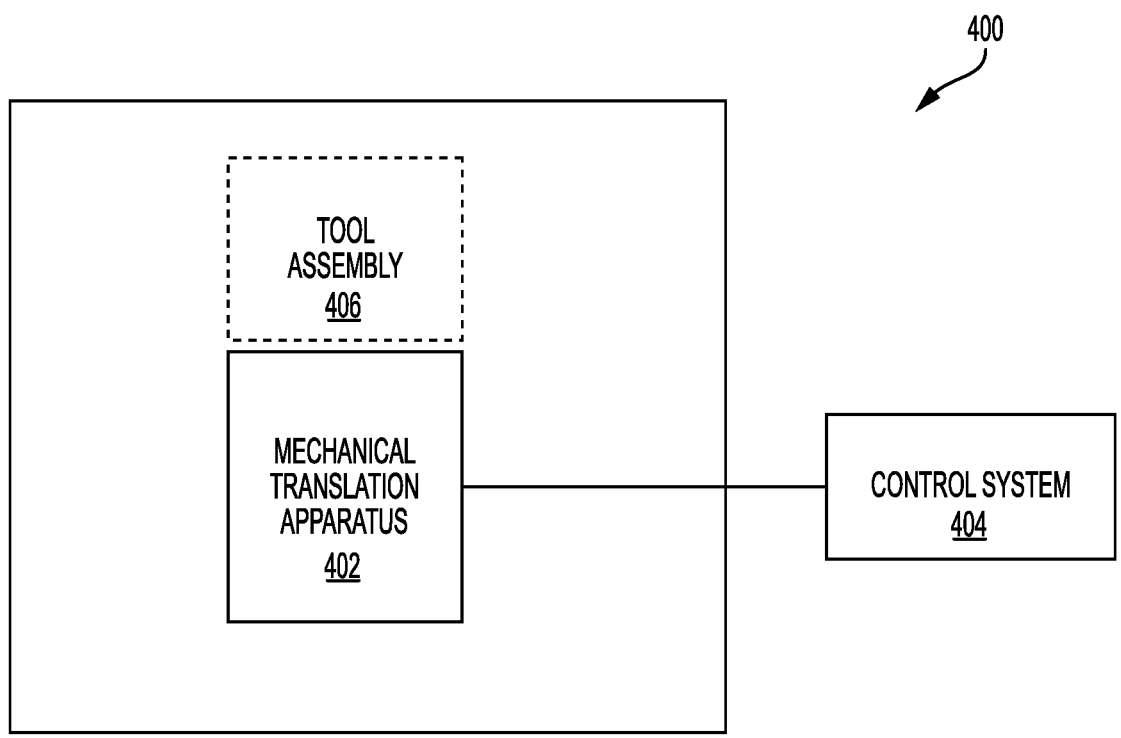
FIG. 18 is a schematic illustration of a teleoperated robot according to an embodiment of the current invention.

FIG. 18 is a schematic illustration of a teleoperated robot 400 according to an embodiment of the current invention. The teleoperated robot 400 has a mechanical translation apparatus 402 and a control system 404 that is at least partially spatially separated from the mechanical translation apparatus 402, for example sufficiently far that the user cannot reach the mechanical translation apparatus 402 while accessing the control system 404. The mechanical translation apparatus 402 can be similar to or the same as mechanical translation apparatus 100 or 200, for example. In some embodiments, the cooperative control robot 400 can also have a tool assembly 406 attached to the translation stage of the translation apparatus (such as, but not limited to, 102 and/or 202) to be carried along with the translation stage.

In addition, the robots may be programmed to perform simple motions under semi-autonomous or supervised control. In this case, the surgeon would manipulate one or both tools to achieve a desired tool-to-tissue relationship and then instruct the robot to make one or more motions autonomously, within a constrained volume, while the surgeon supervises. An example of this behavior might be precise insertion of a needle or injection device to a fixed (small) distance into tissue, stopping if a sensor exceeds a threshold value.

Cooperative control refers to the way the steady hand robots are controlled. Both the surgeon and the robot hold the tool (or the surgeon holds a tool handle attached to the tool). The robot senses forces exerted by the surgeon and moves to comply with the motion. The following references describe some general concepts of cooperative control, all of which are incorporated herein by reference:

R. Kumar, T. Goradia, A. Barnes, P. Jensen, L. Whitcomb, D. Stoianovici, L. Auer, and R. Taylor, "Performance of Robotic Augmentation in Microsurgery-Scale Motions", in 2nd Int. Symposium on Medical Image Computing and Computer-Assisted Surgery, Cambridge, England, Sep. 19-22, 1999. pp. 1108-1115.

R. H. Taylor, P. Jensen, L. L. Whitcomb, A. Barnes, R. Kumar, D. Stoianovici, P. Gupta, Z. X. Wang, E. deJuan, and L. R. Kavoussi, "A Steady-Hand Robotic System for Microsurgical Augmentation", International Journal of Robotics Research, vol. 18-12, 1999.

Kapoor, R. Kumar, and R. Taylor, "Simple Biomanipulation Tasks with a "Steady Hand" Cooperative Manipulator", in Proceedings of the Sixth International Conference on Medical Image Computing and Computer Assisted Intervention—MICCAI 2003, Montreal, Nov. 15-18, 2003. pp. 141-148.

Iordachita, A. Kapoor, B. Mitchell, P. Kazanzides, G. Hager, J. Handa, and R. Taylor, "Steady-Hand Manipulator for Retinal Surgery", in MICCAI Workshop on Medical Robotics, Copenhagen, Oct. 5, 2006. pp. 66-73.

Any of the control modes described above may be modified by "virtual fixtures" to further constrain the motion of the robots. These "virtual fixtures" can be derived from kinematic constraints (e.g., to implement a "virtual remote-center-of-motion" for a tool. Further discussion of methods for providing such virtual fixtures may be found in the following references, all of which are incorporated herein by reference:

J. Funda, R. Taylor, B. Eldridge, S. Gomory, and K. Gruben, "Constrained Cartesian motion control for teleoperated surgical robots", IEEE Transactions on Robotics and Automation, vol. 12-3, pp. 453-466, 1996.

U.S. Pat. No. 5,887,121, J. Funda and R. H. Taylor, "Method of constrained Cartesian control of robotic mechanisms with active and passive joints", Filed Filed Feb. 18, 1999, Issued May 1, 2001.

M. Li and R. H. Taylor, "Spatial Motion Constraints in Medical Robots Using Virtual Fixtures Generated by Anatomy", in IEEE Conf. on Robotics and Automation, New Orleans, April, 2004. pp. 1270-1275.

M. Li, A. Kapoor, and R. Taylor, "A Constrained Optimization Approach to Virtual Fixtures", in IEEE/RSJ Int Conf on Intelligent Robots and Systems (IROS), Edmonton, Alberta, Canada, 2005, pp. 2924-2929

M. Li and R. H. Taylor, "Performance of Teleoperated and cooperatively controlled surgical robots with automatically generated spatial virtual fixtures.", in IEEE International Conference on Robotics and Automation, Barcelona, Spain, 2005

A. Kapoor, N. Simaan, and R. H. Taylor, "Telemanipulation of Snake-Like Robots for Minimally Invasive Surgery of the Upper Airway", in MICCAI Medical Robotics Workshop, Copenhagen, October, 2006. pp. 17-25.

M. Li, M. Ishii, and R. H. Taylor, "Spatial Motion Constraints in Medical Robot Using Virtual Fixtures Generated by Anatomy", IEEE Transactions on Robotics, vol. 23-1, pp. 4-19, 2007.

M. Li, A. Kapoor, and R. H. Taylor, "Telerobot Control by Virtual Fixtures for Surgical Applications". in Advances in Telerobotics Human Interfaces, Bilateral Control and Applications, M. Ferre, M. Buss, R. Aracil, C. Melchiorri, and C. Balaguer, Eds., 2007, pp. 381-401.

A. Kapoor, Motion Constrained Control of Robots for Dexterous Surgical Tasks, Ph.D. thesis in Computer Science, Johns Hopkins University, Baltimore, 2007.

A. Kapoor and R. Taylor, "A Constrained Optimization Approach to Virtual Fixtures for Multi-Handed Tasks", in IEEE International Conference on Robotics and Automation (ICRA), Pasadena, May 19-23, 2008. pp. 3401-3406.

N. Simaan, K. Xu, A. Kapoor, W. Wei, P. Kazanzides, P. Flint, and R. Taylor, "Design and Integration of a Telerobotic System for Minimally Invasive Surgery of the Throat", Int. J. Robotics Research (special issue on medical robotics), vol. 28-9, pp. 1134-1153, June, 2009. http://ijr.sagepub.com/cgi/content/abstract/28/9/1134 DOI 10.1177/0278364908104278, PMC2772168.

Standard surgical instruments could be fitted with adapters so that they could be quickly inserted into and removed from the robot's instrument holder. Some embodiments of the current invention can use carbon fiber, aluminum, and other stiff, lightweight materials, for example. The three translation-driving motors can be implemented using DC servomotors with optical encoders and harmonic gearheads to minimize backlash, for example. The tilt degree of freedom could be implemented using a low backlash screw-based mechanism such as a ball-screw. The roll degree of freedom can be coupled to the drive shaft using a low backlash gear ratio reduction mechanism such as a timing belt, or a chain, for example. If additional reduction is needed, a small harmonic gear box may be used at the end of the drive shaft. The drive shafts can be implemented using spline couplings or ball splines to minimize backlash. Universal joints with needle bearings capable of operating at at least 30 degrees of deflection can be used on the ends of the drive shafts.

In other embodiments, it can also be possible to remotely teleoperate the system using a master such as the daVinci console or locally teleoperate it using simpler devices such as a Phantom Omni or joystick. In this case, it can be possible to use the built-in force sensor to provide force feedback of tool forces to the surgeon.

In other embodiments, it can also be possible to integrate custom high-dexterity instruments, such as the wristed instruments that the daVinci system uses, rather than existing surgical instruments.

In other embodiments, more degrees of freedom can be added using additional drive shafts, small motors directly on the end effector, or some other power transmission method, such as pneumatics, for example.

The drive shafts can be configured in other ways, such as with two concentric shafts, or both drive shafts off center coupled with chains, belts or cables to the tilt/roll mechanisms.

Other power transmission methods from shafts to the tilt/roll mechanisms can be used (chains, gears, cables, belts, etc.).

The tilt mechanism can be implemented in many ways, such as a 4-bar linkage driven by a linear actuator as illustrated in the drawings, a linkage driven by a rotary actuator, or directly driven by a rotary actuator using a chain, cable, pulley, or other coupling. A remote center of motion linkage such as in the Eye Robot 2 can also be used.

In other embodiments, additional robotic tool control assemblies can be added to provide robotic assistance to more than one user, or to provide control of more instruments for one user.

An additional robot can be added to control a visualization device, such as a flexible or rigid endoscope.

Figure 1:
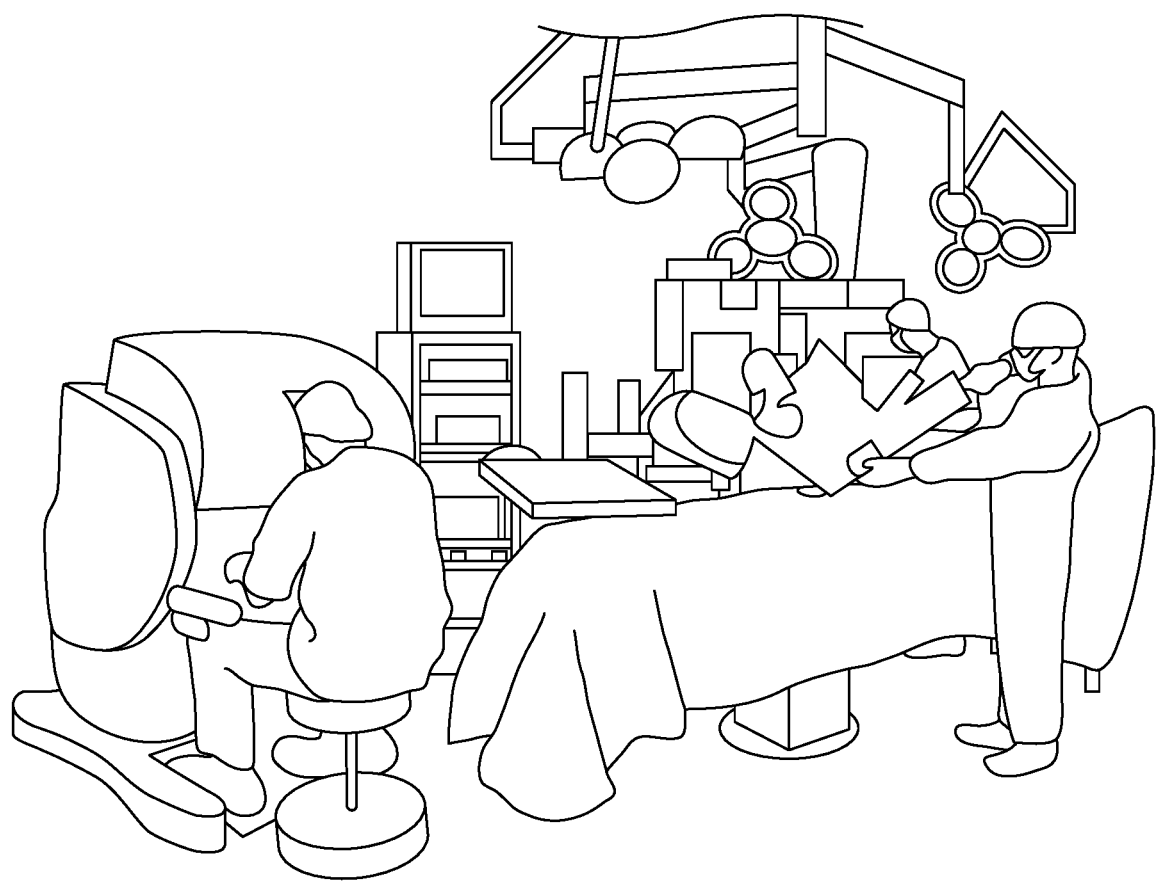
FIG. 1 shows an example of the daVinci robotic system from Intuitive Surgical.
Figure 2:
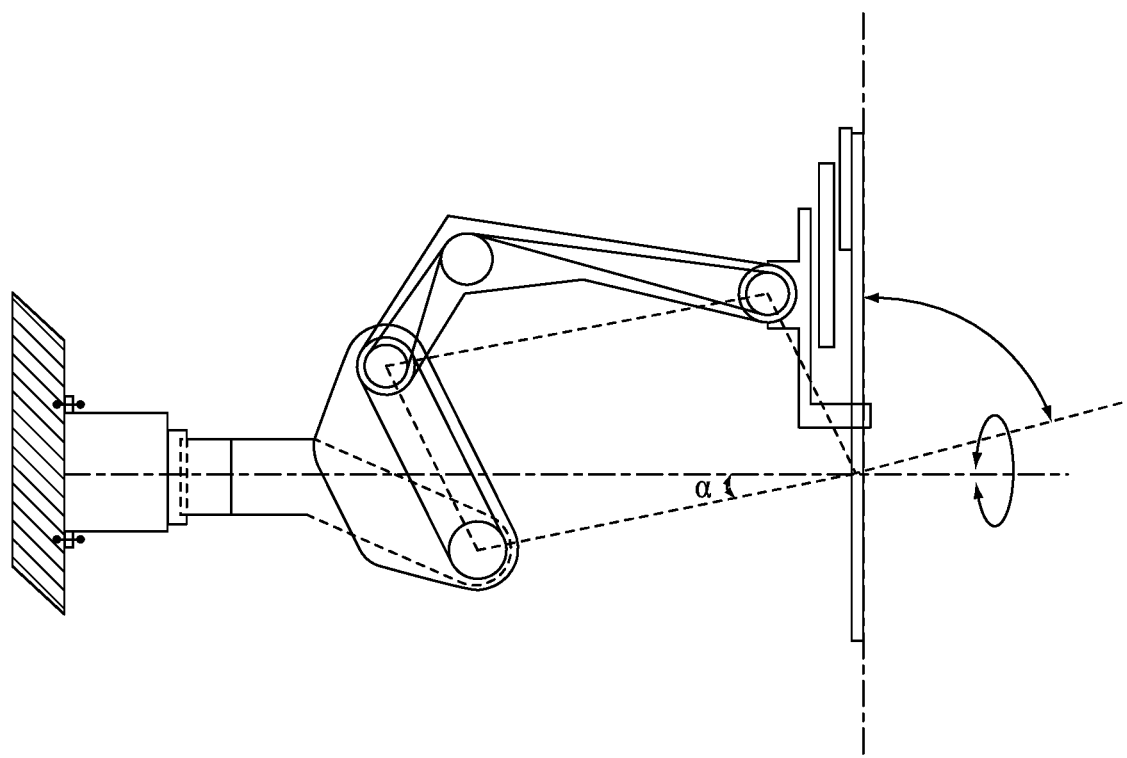
FIG. 2 illustrates the daVinci remote center of motion mechanism[1].
Figure 3:
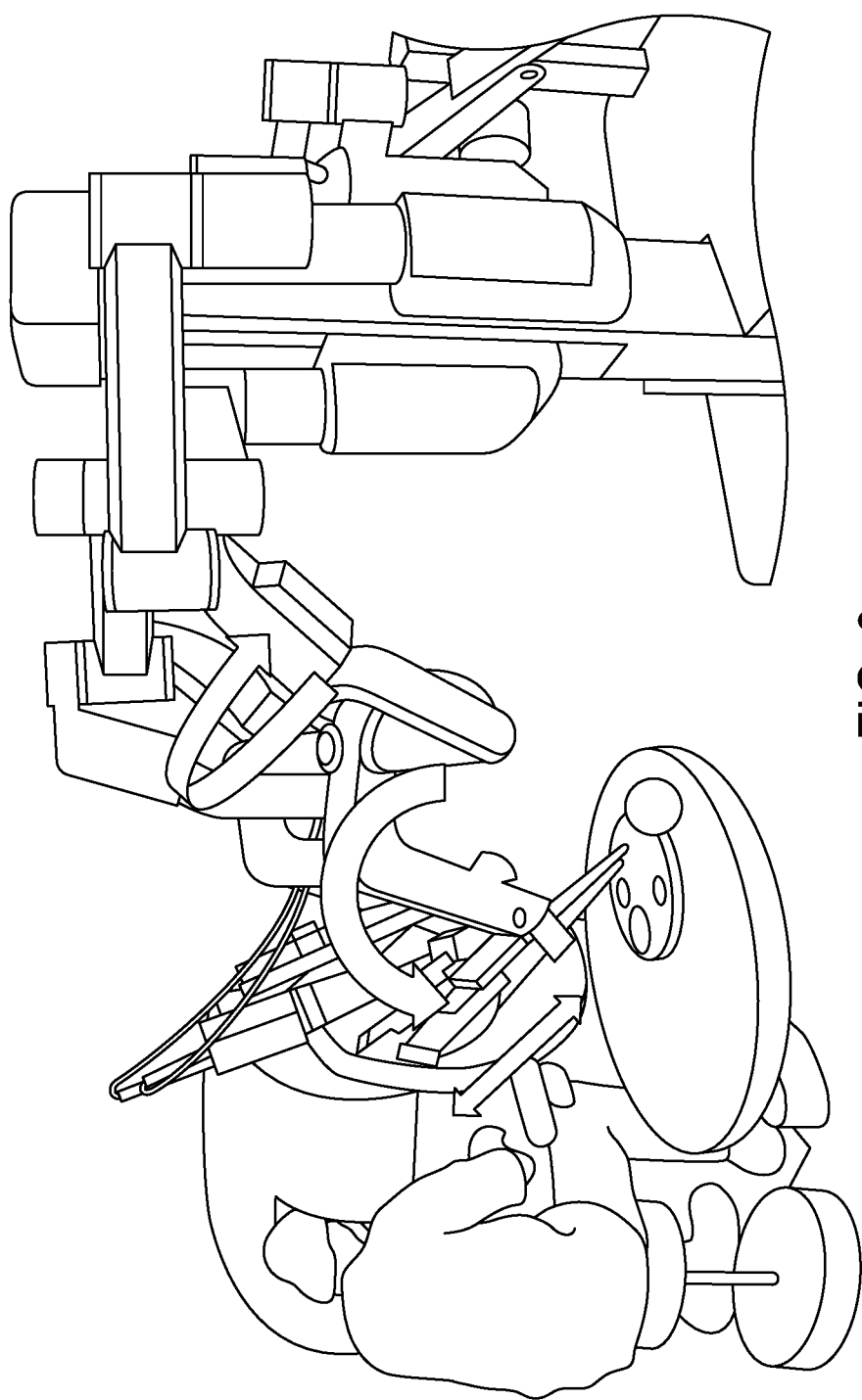
FIG. 3 shows an example of the daVinci degrees of freedom. (straight, two-headed arrow: insertion/extraction translation stage. Lower, curved arrow: Tilt. Upper, curved arrow: Roll.)
Figure 4:
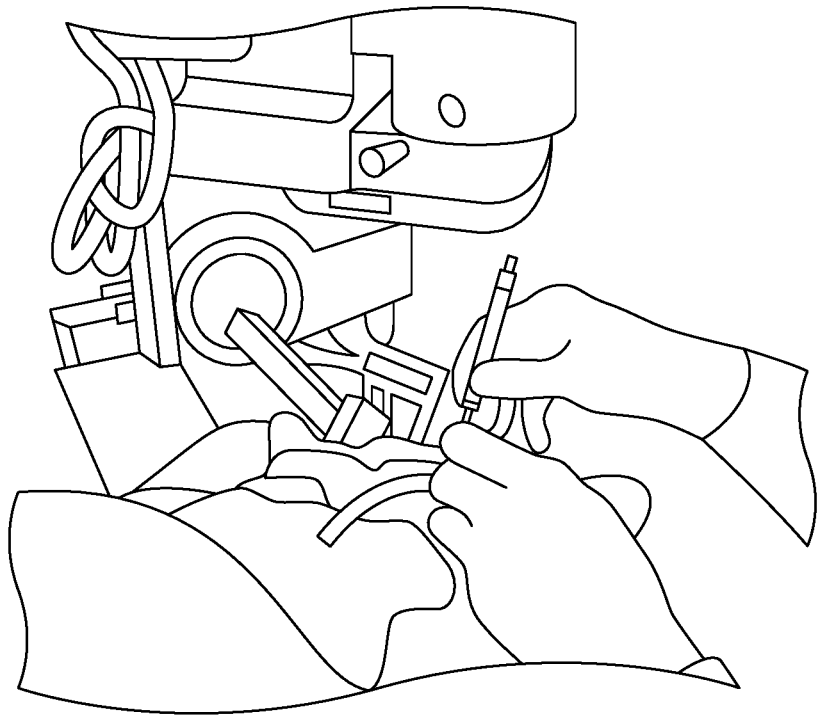
FIG. 4 shows an example of the JHU Eye Robot 2.
Figure 4:
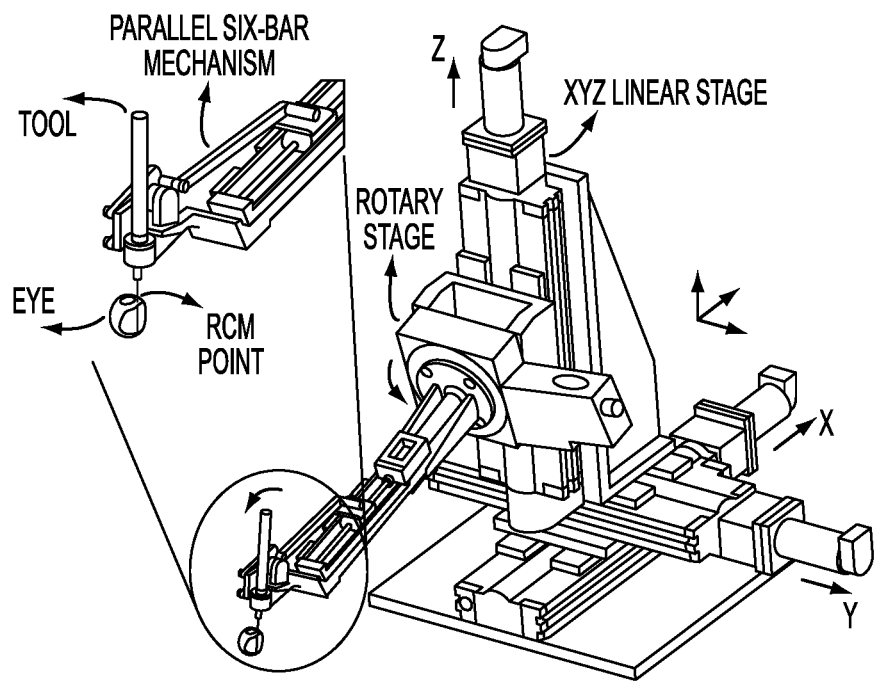
Figure 5:
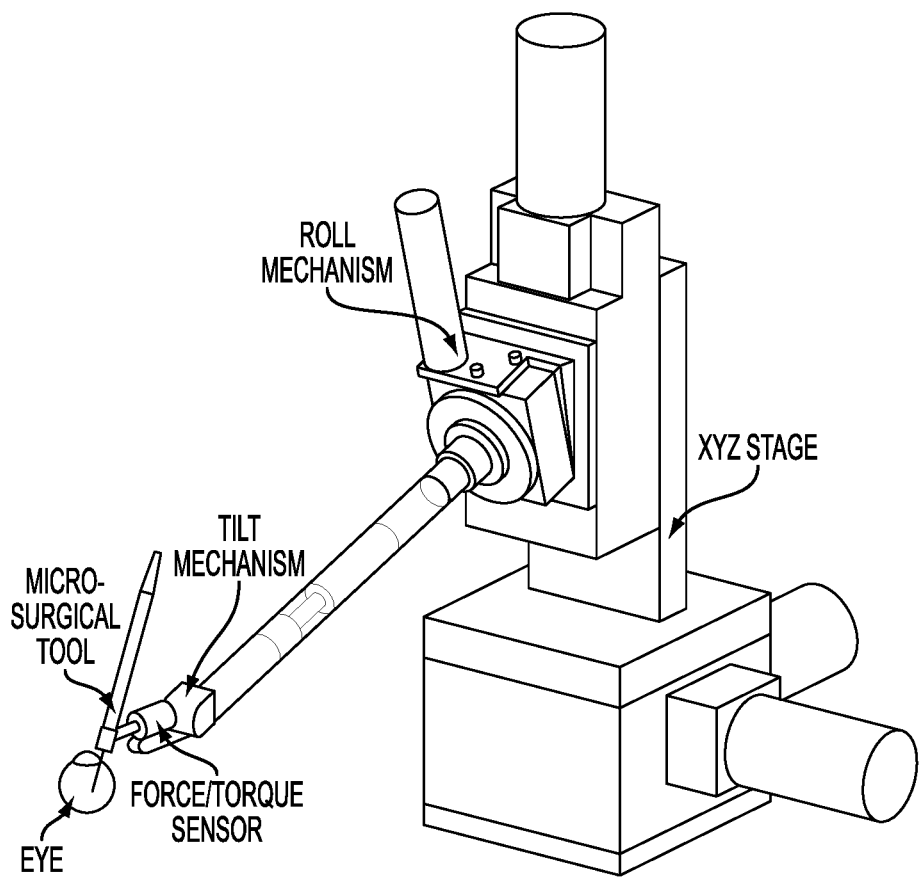
FIG. 5 shows an example of the JHU Eye Robot 1.
Figure 6:
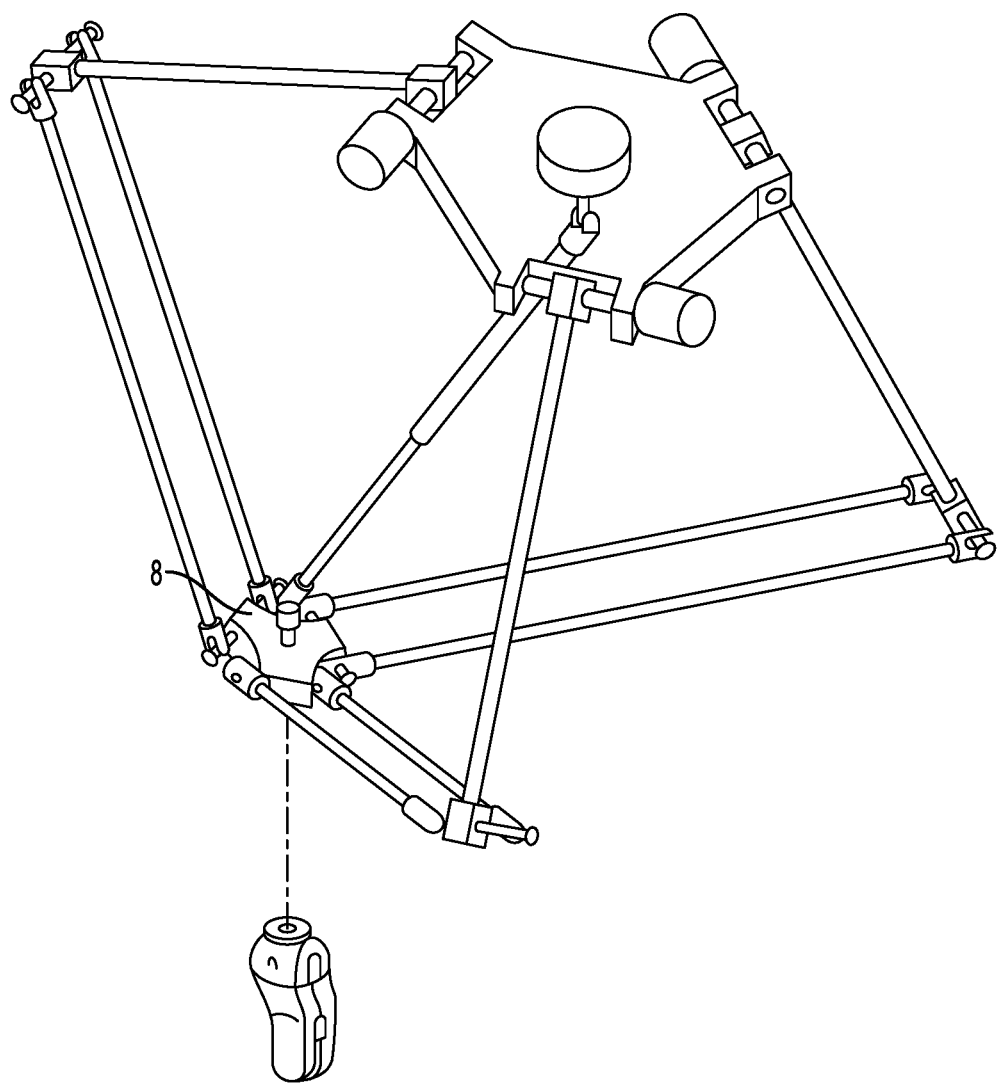
FIG. 6 is a drawing of a delta mechanism[3].
Figure 7:
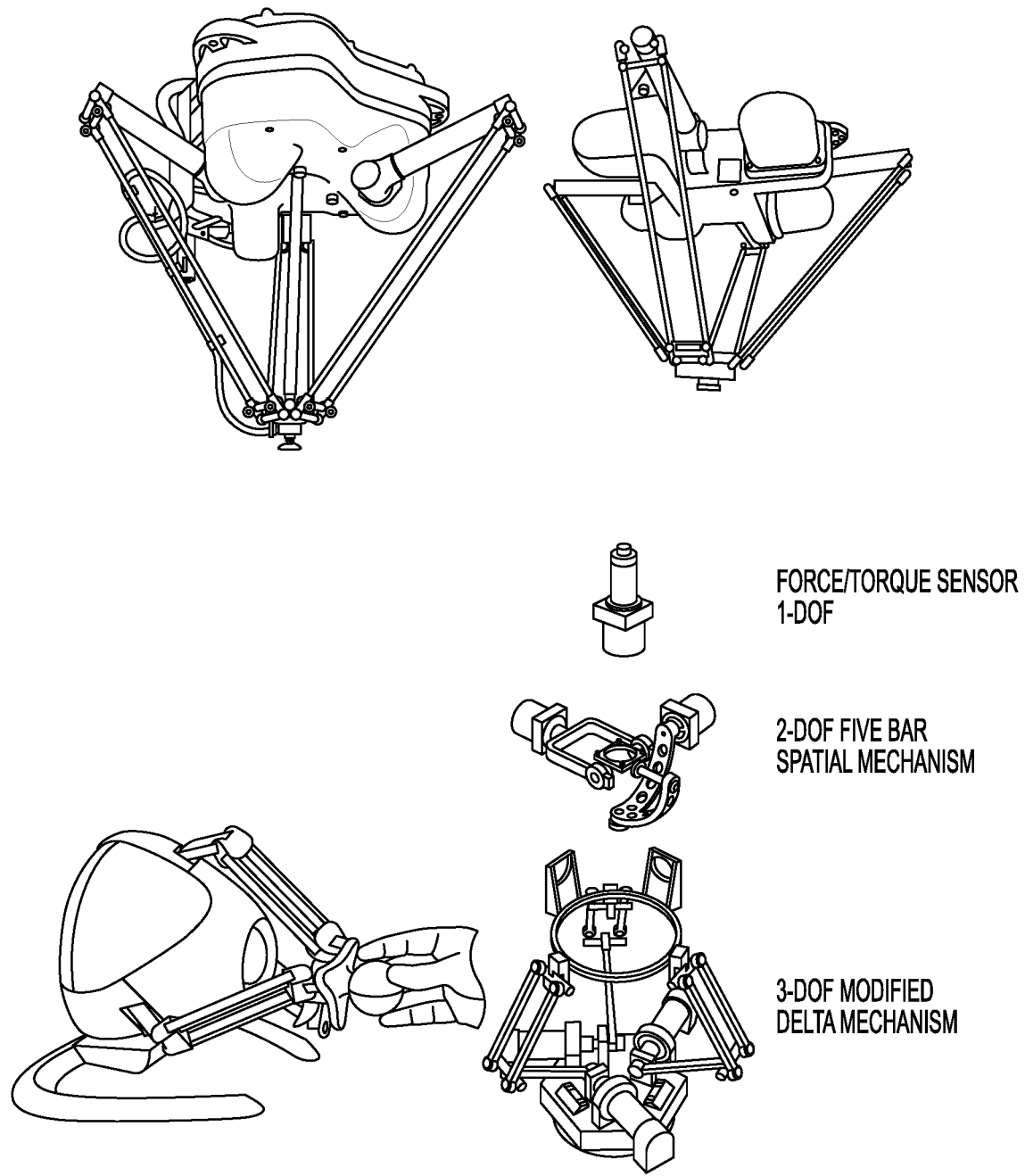
FIG. 7 shows examples of: Top Left, Industrial delta robot[4]; Top Right, The Adept Quattro, a four link delta robot; Bottom Left, Commercial haptic master using delta mechanism; Bottom Right, 6 dof haptic master.[5]
Figure 8:
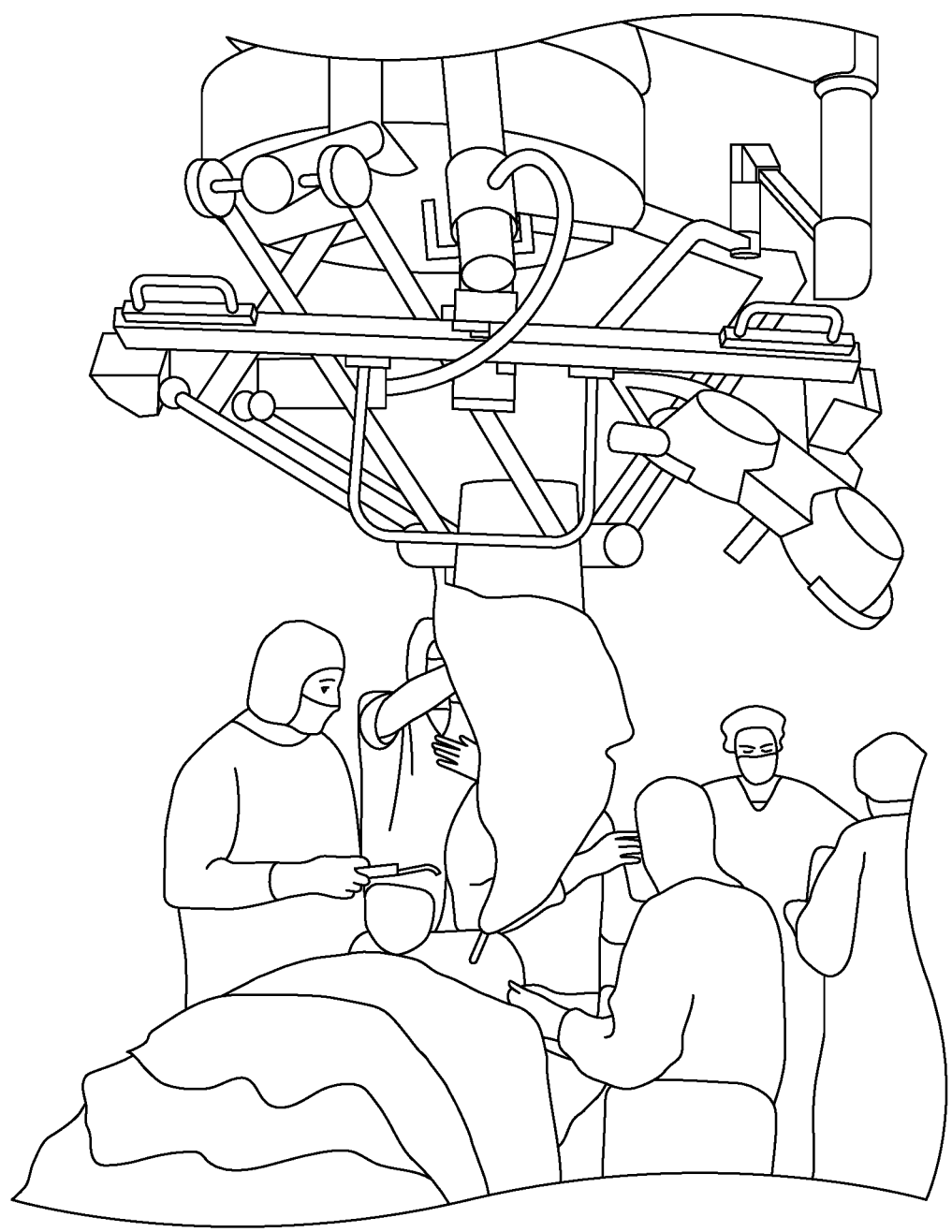
FIG. 8 show an example a delta robot for maxillofacial surgery.
Figure 9:
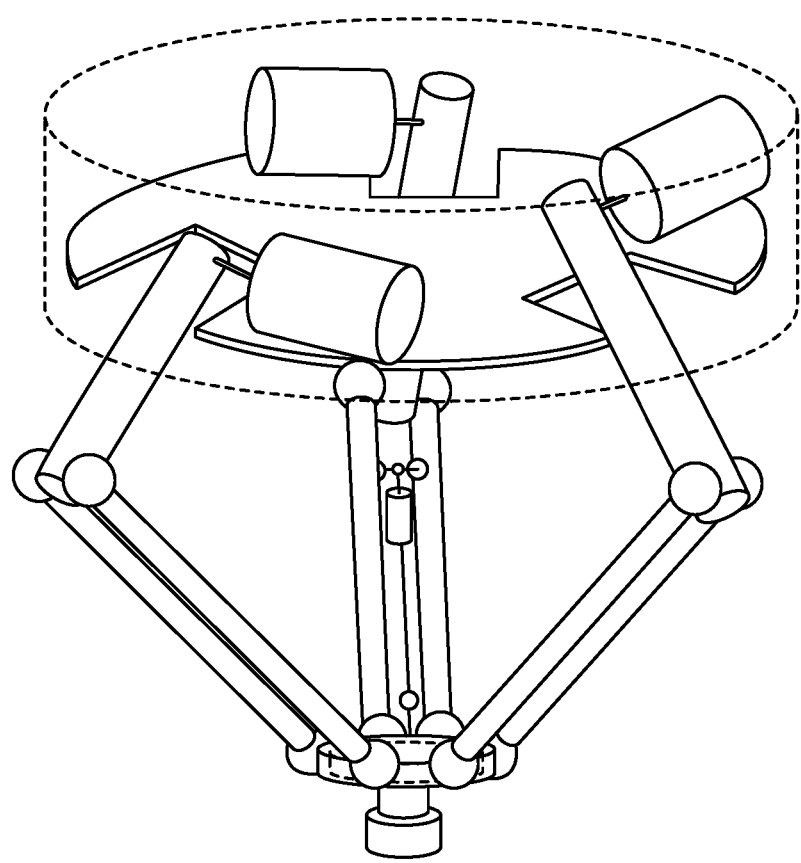
FIG. 9 is a schematic illustration of a modified delta mechanism with three actuators mounted on the robot's legs.
Figure 10:
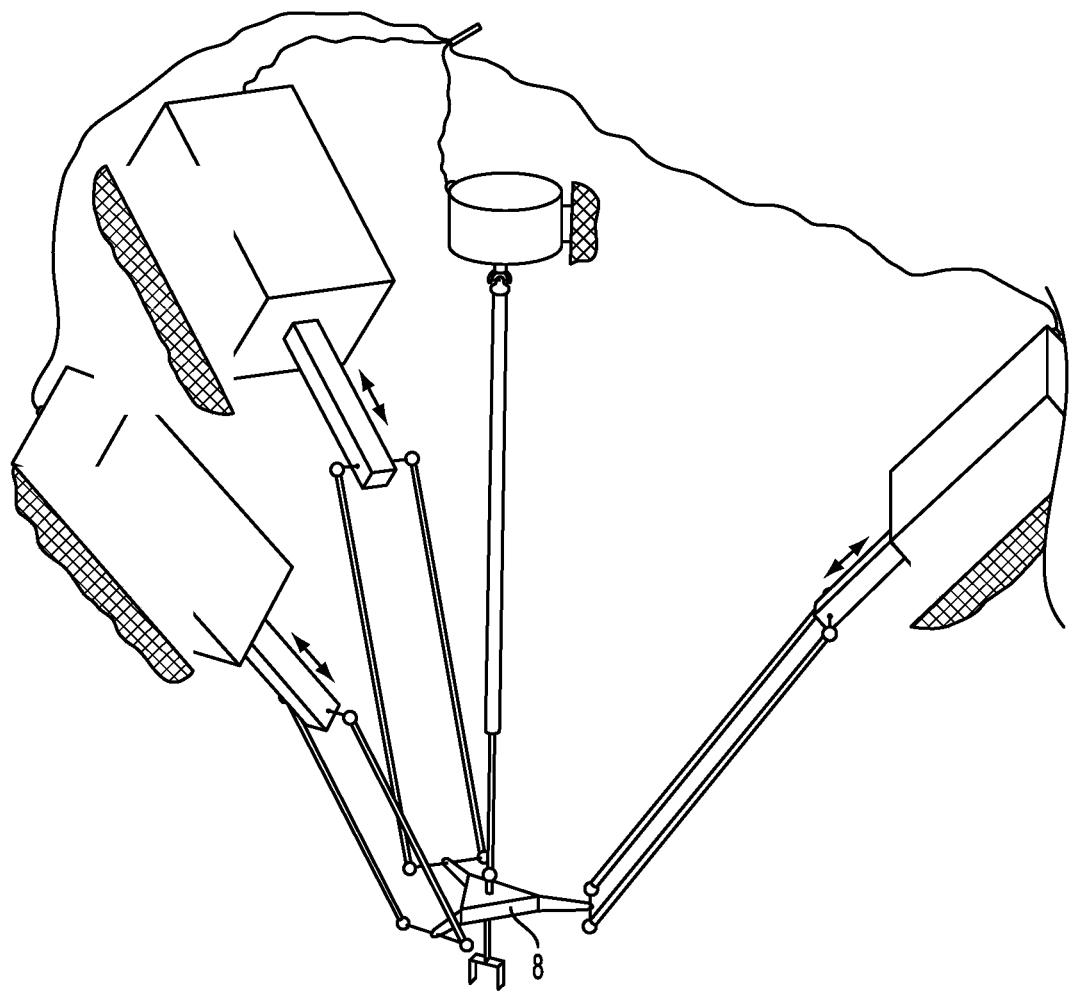
FIG. 10 is an illustration of a linear variant of the delta robot.[3]

For added rigidity, it would also be possible to implement the delta mechanism in the actuators with four links, as in the Adept Quattro (FIG. 7 Mid Left).

Depending on the application, it may be geometrically advantageous to use the linear variant of the delta mechanism in the robots.

REFERENCES

1. Cooper et al. "Offset remote center manipulator for robotic surgery." U.S. Pat. No. 7,594,912. 29 Sep. 2009.
2. Taylor, Russell et al. "Remote center-of-motion robot for surgery." U.S. Pat. No. 5,397,323. 30 Oct. 1992.
3. Clavel, Reymond. "Device for the movement and positioning of an element in space." U.S. Pat. No. 4,976,582. 11 Dec. 1990.
4. Ilian Bonev. "Delta Parallel Robot—the Story of Success." http://www.parallemic.org/Reviews/Review002.html. May 2001.
5. Y. Tsumaki, H. Naruse, D. N. Nenchev, and M. Uchiyarna. Design of a Compact 6-DQF Haptic Interface. Proceedings of the 1998 IEEE International Conference on Robotics & Automation Leuven, Belgium—May 1998
6. Leuth et al. "A surgical robot for maxillofacial surgery." IEEE Industrial Electronics Conference. 1998.
7. Kinoshita et al. "Parallel Link Robot." US Patent 2011/0097184 A1. Apr. 28, 2011.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A mechanical translation apparatus, comprising:
a translation stage; and
a translation assembly operatively connected to said translation stage so as to impart linear motions to said translation stage, wherein said translation assembly comprises a plurality of at least three arms pivotably connected to said translation stage at a first end of each arm of said plurality of at least three arms; and
a base assembly wherein each arm is rotationally connected thereto at a second end of each arm,
wherein each arm of said plurality of at least three arms comprises three rigid elongate structures arranged substantially parallel and non-coplanar with respect to each other so as to act in cooperation to cancel torques so that substantially purely linear motion is imparted to said translation stage by said plurality of at least three arms, and
wherein said translation assembly constrains motion of said translation stage to be substantially purely translational motion free of rotational motion,
wherein said base assembly comprises three substantially parallel, non-coplanar track assemblies extending from a base structure, wherein each of said three track assemblies is configured to receive a corresponding one of said arms of said plurality of at least three arms such that each arm is slidable along a respective track of said track assemblies as well as being rotatable about an axis substantially orthogonal to a direction of said track extending from said base structure.

2. The apparatus of claim 1, wherein said base assembly comprises a secondary track arm corresponding to each of said at least three arms of said translation assembly, each secondary arm being rotationally connected at one end to a corresponding arm in the at least three arms and rotationally connected at a second end to a base structure of said base assembly.

3. The apparatus of claim 2, wherein each said secondary arm comprises a pair of substantially parallel elongate structures.

4. A robot, comprising:
a translation stage;
a translation assembly operatively connected to said translation stage so as to impart linear motions to said translation stage, wherein said translation assembly comprises a plurality of at least three arms pivotably connected to said translation stage at a first end of each arm of said plurality of at least three arms;
a base assembly wherein each arm is rotationally connected thereto at a second end of each arm; and
a control system configured to communicate with said translation assembly to control motion of said translation stage in response to commands by a user,
wherein each arm of said plurality of at least three arms comprises three rigid elongate structures arranged substantially parallel and non-coplanar with respect to each other so as to act in cooperation to cancel torques so that substantially purely linear motion is imparted to said translation stage by said plurality of at least three arms, and
wherein said translation assembly constrains motion of said translation stage to be substantially purely translational motion free of rotational motion,
wherein said base assembly comprises three substantially parallel, non-coplanar track assemblies extending from a base structure, wherein each of said three track assemblies is configured to receive a corresponding one of said arms of said plurality of at least three arms such that each arm is slidable along a respective track of said track assemblies as well as being rotatable about an axis substantially orthogonal to a direction of said track extending from said base structure.

5. The robot of claim 4, further comprising a tool assembly attached to said translation stage.

6. The robot of claim 5, further comprising a force sensor in at least one of said tool assembly, said translation stage or said translation assembly arranged to detect a force applied by a user to a portion of said robot,
wherein said force sensor is further configured to be in communication with said control system to provide detection signals thereto, and
wherein said control system is configured to provide control signals to move said translation stage in cooperative control with said user based on forces applied by said user to said portion of said robot.

7. The robot of claim 6, wherein said control system is further configured to provide signals for semiautonomous control based on force signals by said user.

8. The robot of claim 4, wherein said control system is at least partially spatially separated from said translation stage and said translation assembly out of reach of a user and is further configured to provide control signals to move said translation stage by teleoperative control by said user.

9. The robot of claim 8, wherein said control system is further configured to provide signals for semiautonomous control based on teleoperative control signals by said user.

10. The robot of claim 4, wherein said base assembly comprises a secondary arm corresponding to each of said at least three arms of said translation assembly, each secondary arm being rotationally connected at one end to a corresponding arm in the at least three arms and rotationally connected at a second end to a base structure of said base assembly.

11. The robot of claim 10, wherein each said secondary arm comprises a pair of substantially parallel elongate structures.

12. The robot of claim 4, wherein said control system is further configured to provide signals for at least one of autonomous or semiautonomous control.

\* \* \* \* \*